United States Patent [19]

Bowman et al.

[11] Patent Number: 5,118,851
[45] Date of Patent: Jun. 2, 1992

[54] PROCESS OF PREPARING MIXTURES OF POLYALKYLENEPOLYAMINES AND ALKANOLPOLYAMINES

[76] Inventors: Robert G. Bowman, 1307 Kirkland; David C. Molzahn, 5501 Corland St.; George E. Hartwell, 2908 Georgetown, all of, Midland, Mich. 48640

[21] Appl. No.: 622,444

[22] Filed: Dec. 5, 1990

Related U.S. Application Data

[63] Continuation of Ser. No. 370,316, Jun. 21, 1989, abandoned.

[51] Int. Cl.$^5$ ............................................. C07C 209/00
[52] U.S. Cl. ........................................ 564/479; 502/240; 502/250; 502/251; 564/346; 564/349; 564/355; 564/372; 564/401; 564/402; 564/474
[58] Field of Search .............. 564/479, 346, 349, 355, 564/372, 401, 402, 474; 502/251, 240, 250

[56] References Cited

U.S. PATENT DOCUMENTS

| | | | |
|---|---|---|---|
| 2,394,516 | 2/1946 | Goshom | 564/480 |
| 2,412,209 | 12/1946 | Dickey et al. | 564/479 |
| 2,985,658 | 5/1961 | Krause | 544/352 |
| 3,714,259 | 1/1973 | Lichtenwalter et al. | 564/480 |
| 4,314,083 | 2/1982 | Ford et al. | 564/479 |
| 4,495,369 | 1/1985 | Werner et al. | 564/479 |

Primary Examiner—Glennon H. Hollrah
Assistant Examiner—Scott C. Rand

[57] ABSTRACT

A process of preparing a mixture of polyalkylenepolyamines and alkanolpolyamines comprising contacting a difunctional aliphatic alcohol with a primary or secondary aliphatic amine in the presence of a metal silicate catalyst wherein the metal is selected from the group consisting of Groups IIA, IIIB, and the lanthanide and actinide metals. For example, monoethanolamine reacts with diethylenetriamine in the presence of magnesium silicate to yield a mixture of higher molecular weight linear and branched polyethylenepolyamines and their corresponding alkanolpolyamines. These product mixtures are useful in the formation of specialty polyurethanes.

25 Claims, No Drawings

PROCESS OF PREPARING MIXTURES OF POLYALKYLENEPOLYAMINES AND ALKANOLPOLYAMINES

This application is a continuation of Ser. No. 370,316, filed Jun. 21, 1989, now abandoned.

BACKGROUND OF THE INVENTION

This invention relates to a process for preparing mixtures of polyalkylenepolyamines and alkanolpolyamines.

Mixtures of polyalkylenepolyamines and alkanolpolyamines find utility in the formation of urethane polymers. Typically, polymers produced with these mixtures exhibit rates of polymerization which are different from the rates produced with either alkanolpolyamines or polyalkylenepolyamines alone. Since the physical properties of urethane polymers can vary with rate of polymerization, a broader spectrum of polymer properties is available from the use of mixtures of polyalkylenepolyamines and alkanolpolyamines.

It is known that polyalkylenepolyamines can be prepared by the reaction of an alkyl halide with ammonia or an amine. The product is a polyalkylenepolyamine hydrohalide salt, which must be neutralized with base in order to recover the valuable polyalkylenepolyamine product. Disadvantageously, the neutralization produces a waste stream of metal salt, which must be removed. More disadvantageously, the process does not coproduce alkanolpolyamines. Even more disadvantageously, the process producess considerable amounts of undesirable cyclic compounds, such as piperazine.

It is known that salt-free non-cyclic polyethylenepolyamines can be directly prepared by reacting ammonia with an ethanolamine in the presence of hydrogen and a hydrogenation catalyst. For example, U.S. Pat. No. 3,766,184 discloses such a process with catalysts of nickel, iron, and cobalt supported on a variety of supports, including inorganic silicates. U.S. Pat. No. 3,270,059 teaches the amination of alkanediols and alkanolamines with primary or secondary amines to diaminoalkanes in the presence of Group IB and Group VIII metals in admixture with carrier substances, such as synthetic or natural silicates. These processes produce only the lower polyalkylenepolyamines, and in certain examples substantial quantities of cyclics, such as piperazine. Disadvantageously, the process does not coproduce the higher homologues of polyalkylenepolyamines and the corresponding alkanolpolyamines.

More recently it is known to prepare non-cyclic polyalkylenepolyamines directly by reacting an alkanolamine with an alkyleneamine under non-reductive conditions, that is, in the absence of hydrogen. Many of the non-reductive aminations are known to employ a phosphorous containing catalyst. U.S. Pat. No. 4,555,582, for example, teaches the use of a thermally activated pelleted catalyst composition comprising zirconium silicate having phosphorous deposited thereon for the reaction of ethylenediamine with monoethanolamine. These processes do not coproduce significant amounts of higher molecular weight alkanolpolyamines. For instance, the triethylenetetramine fraction does not contain the corresponding hydroxy compounds, such as hydroxyethyldiethylenetriamine. Moreover, the phosphorus-component of these catalysts can leach into the reaction causing catalyst deactivation and separation problems.

Other non-reductive processes are known employing phosphorus-containing catalysts. U.S. Pat. No. 4,463,193, for example, discloses the production of non-cyclic polyalkylenepolyamines by reacting an alkanolamine with an alkyleneamine and ammonia in the presence of a Group IIIB metal acid phosphate, including the rare earth lanthanide metals. These processes do not coproduce significant quantities of higher molecular weight alkanolpolyamines. Moreover, the phosphorus-containing catalysts lose their physical integrity in the presence of water, which is a by-product of the amination reaction. In addition, the catalysts can react with water to release free phosphoric acid or amine phosphate salts, thereby losing their phosphorus component. Consequently, these catalysts can plug reactors or leach into the reaction mixture causing catalyst losses and separation problems.

Currently, therefore, the preparation of mixtures of polyalkylenepolyamines and alkanolpolyamines is a multi-step process. Consider, for instance, how one skilled in the art would prepare a mixture of triethylenetetramine and hydroxyethyldiethylenetriamine. First, triethylenetetramine and diethylenetriamine would be prepared either independently or as a mixture by any of the above-identified processes. Next, the isolated diethylenetriamine would be reacted with ethylene oxide to prepare hydroxyethyldiethylenetriamine. Finally, the mixture of triethylenetetramine and hydroxyethyldiethylenetriamine would be prepared in the desired weight ratio.

It would be advantageous to have an amination process which produces mixtures of higher molecular weight polyalkylenepolyamines and alkanolpolyamines from lower molecular weight alkylenepolyamines and alkanolamines. It would be more advantageous if the process is accomplished in one-step and does not produce a waste stream of metal salts. It would be even more advantageous if the catalyst for such a process is insoluble in the liquid reactants. It would be most advantageous if the catalyst for such a process retains its physical integrity in the presence of water. Such a process would eliminate problems with catalyst leaching, reactor plugging, and catalyst separation. A process having all of these attributes would operate at a considerable cost advantage over current technologies required to prepare such mixtures.

SUMMARY OF THE INVENTION

This invention is a process for preparing a mixture of polyalkylenepolyamines and alkanolpolyamines comprising contacting a reactant mixture containing a difunctional aliphatic alcohol and a primary or secondary aliphatic amine with a catalytic amount of a metal silicate. The metal of the metal silicate catalyst is selected from the group consisting of Groups IIA, IIIB, and the lanthanide and actinide metals of the Periodic Table. The contacting is conducted under reaction conditions such that a product mixture of polyalkylenepolyamines and alkanolpolyamines is produced, such that the average molecular weight of the product mixture is higher than the average molecular weight of the reactant mixture.

Advantageously, the process of this invention produces, in one step, mixtures of higher molecular weight polyalkylenepolyamines and alkanolpolyamines. More advantageously, the process of this invention does not produce a waste stream of metal salts. Even more advantageously, the catalyst employed in this process is insoluble in the amine and alcohol reactants; therefore, catalyst losses are minimized and separation of the product mixture from the catalyst is relatively easy. Most advantageously the catalyst employed in this process retains its physical integrity in the presence of water. Consequently, the catalyst possesses a long lifetime and is suitable for industrial use.

The mixtures containing polyalkylenepolyamines and alkanolpolyamines, which are produced by the process of this invention, are useful as dispersants, surfactants, chelants, curing agents, and catalysts, and are especially useful in the formation of urethane polymers.

DETAILED DESCRIPTION OF THE INVENTION

The difunctional aliphatic alcohols which are employed in the process of this invention include any aliphatic alcohol containing (a) at least one hydroxyl moiety bound to a primary carbon atom, and (b) at least one additional moiety selected from the group consisting of hydroxyl, primary amine or secondary amine functionalities. Examples of suitable difunctional aliphatic alcohols include diols such as ethylene glycol and propylene glycol, triols such as glycerol, and higher polyols; polyether polyols such as diethylene glycol, polypropylene glycol, and higher homologues; alkanolamines such as ethanolamine and N-(2-aminoethyl)ethanolamine; and polyether amino alcohols such as 2-($\beta$-aminoethoxy)ethanol. The difunctional alcohols are not limited to the aforementioned examples, and other equally suitable difunctional alcohols can be employed in the practice of this invention.

Preferably, the difunctional alcohols are represented by the general formula:

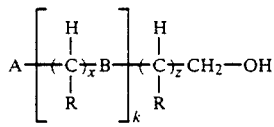

wherein A is OH or NHR; each B is independently NR or O; each R is independently hydrogen, hydroxyl, amino (NH$_2$), an alkyl moiety of C$_1$-C$_{12}$ carbon atoms such as methyl, ethyl or propyl, a hydroxyalkyl or aminoalkyl moiety of C$_1$-C$_{12}$ carbon atoms, or a monocyclic aromatic moiety, such as phenyl, or tolyl; x is an integer from 2 to about 12; k is an integer from 0 to about 150; and z is an integer from 1 to about 12. Preferably, R is hydrogen. More preferably, R is hydrogen, x is 2, and z is 1. Most preferably, R is hydrogen, A is NH$_2$, k is 0, z is 1, and the difunctional aliphatic alcohol is monoethanolamine.

The aliphatic primary or secondary amines which are employed in the process of this invention include any which are capable of aminating the difunctional aliphatic alcohol. Examples of suitable aliphatic amines include monoamines, such as ethylamine, propylamine, n-butylamine, hexylamine, octylamine, diethylamine, dipropylamine, dibutylamine, dihexylamine, dicyclohexylamine, and dioctylamine; linear and branched alkylene diamines or polyamines such as ethylenediamine, propylenediamine, diethylenetriamine, triethylenetetramines, and tetraethylenepentamines; alkylene ether polyamines such as 2-($\beta$-aminoethoxy)ethylamine; and mixtures of the above-identified amines. While the aforementioned amines are representative of those which are suitable in the process of this invention, other aliphatic primary and secondary amines not recited herein may be equivalent and equally suitable.

Simple primary and secondary amines which are preferred for the process of this invention are represented by the general formula R$^1{}_2$NH, wherein each R$^1$ is independently hydrogen or a C$_1$-C$_{12}$ alkyl moiety. Preferably, the alkylenepolyamines and alkylene ether polyamines which are suitable in the process of this invention are represented by the general formula:

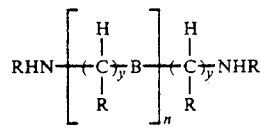

wherein each B is independently NR or O; each R is independently hydrogen, hydroxyl, amino, an alkyl moiety of C$_1$-C$_{12}$ carbon atoms, a hydroxyalkyl or aminoalkyl moiety of C$_1$-C$_{12}$ carbon atoms, or a monocyclic aromatic moiety; each y is independently an integer from 2 to about 12, and n is an integer from 0 to about 150. Preferably, each B is NR and the amine is an alkylenepolyamine. More preferably, the amine is an alkylenepolyamine and each R is hydrogen. Even more preferably, B is NR, R is hydrogen, each y is 2, and the amine is an ethylenepolyamine. Most preferably, the reactant amine is ethylenediamine.

Typically, as the mole ratio of alkyleneamine to difunctional alcohol varies, the quantity of hydroxycontaining compounds in the product mixture also varies. Thus, any mole ratio of reactant amine to difunctional aliphatic alcohol is suitable provided that the ratio enables the amination reaction to proceed to the desired polyalkylenepolyamine and alkanolpolyamine mixture. Usually, the alcohol is reacted with at least about one mole equivalent of reactant amine; however, an excess of reactant amine can be advantageously employed. Preferably, the mole ratio of reactant amine to difunctional aliphatic alcohol is in the range from about 0.1 to about 20. More preferably, the mole ratio of reactant amine to difunctional aliphatic alcohol is in the range from about 1 to about 15; most preferably from about 2 to about 10.

Although, preferably, a solvent is not used in the amination reaction, it is within the scope of the invention for a solvent to be used, if desired. Any solvent is acceptable provided that (1) it is not reactive with the difunctional alcohol and the reactant or product amines, and (2) it does not decompose under the conditions of the reaction. Some examples of suitable solvents include water, saturated aliphatic hydrocarbons such as pentane, hexane, heptane, octane, nonane, and decane, and aromatic hydrocarbons such as benzene, toluene, and xylene. The amount of solvent employed depends upon the particular reactants and reaction conditions. Any amount of solvent is acceptable that meets the intended purpose of use. Typically, the solvent constitutes from about 5 weight percent to about 95 weight percent of the feed stream. Preferably, the solvent constitutes from about 10 weight percent to about 80 weight percent of the feed stream.

In accordance with the process of this invention, the amination reaction is conducted in the presence of a catalyst comprising a metal silicate. The metal silicate is any which is not readily reducible to elemental metal. Preferably, the metal of the metal silicate is selected from Groups IIA, IIIB, and the lanthanide and actinide metals of the Periodic Table. Preferably, the metal of the metal silicate is beryllium, magnesium, calcium, strontium, barium, actinium, thorium, protactinum, uranium, scandium, yttrium, lanthanum, praeseodymium, or europium. More preferably, the metal of the metal silicate is magnesium, thorium, yttrium, or lanthanum. Most preferably, the metal of the metal silicate is magnesium or thorium. The metal silicate can be employed in an amorphous form containing a distribution of silicate anions of various sizes. Alternatively, the metal silicate can be employed in a crystalline form, such as the siliceous zeolite structure exhibited by sodium magnesium silicate.

The mole ratio of silicon to metal will vary in the metal silicate depending upon the metal cation, its valence, and the form of the silicate anion. For instance, in the case of magnesium silicate, the preferred silicon to magnesium mole ratio varies from about 0.5 to about 20. More preferably, the silicon to magnesium mole ratio varies from about 1 to about 10, most preferably, from about 1 to about 5. Other metal silicates may exhibit silicon to metal mole ratios which are different from the preferred ratios shown here for magnesium silicate.

In a preferred form, the metal silicate catalyst which is employed in the process of this invention is essentially free of aluminum and the metals of Groups IB (Cu, Ag, Au) and VIII of the Periodic Table. The term "essentially free of" is taken to mean that the metal silicate contains less than about 5 weight percent of each of aluminum, and the metals of Groups IB and VIII. Preferably, the metal silicate contains less than about 3 weight percent of each of aluminum and the metals of Groups IB and VIII. More preferably, the metal silicate contains less than about 1 weight percent of each of aluminum and the metals of Groups IB and VIII.

The common metal silicates which are employed in the process of this invention are commercially available. The less common silicates, such as thorium silicate, may be prepared by methods reported in *The Colloid Chemistry of Silica and Silicates* by Ralph K. Iler, Cornell University Press, 1955; or in *The Chemistry of Silica: Solubility, Polymerization, Colloid and Surface Properties, and Biochemistry* by Ralph K. Iler, John Wiley & Sons, 1979; and references therein.

The metal silicate catalyst can be prepared by a variety of synthetic methods. One, for example, requires the formation of a mixture of silica ($SiO_2$) with the oxide of the desired metal. The oxide mixture is calcined at a temperature sufficient to form the desired metal silicate. Another method, for example, depends upon the hydrolysis of mixtures of tetra(ethoxy)silicon and an alkoxide of the desired metal, e.g., magnesium ethoxide. The hydrolysis reaction yields the desired metal silicate.

Preferably, however, the metal silicates are prepared by direct precipitation from a mixture of two aqueous solutions. One of these solutions contains a soluble silicate salt, such as sodium silicate. Typically, the soluble silicate salt is dissolved in a minimum amount of water. Typically, the solution is heated, preferably to boiling, to aid in the dissolution of the salt. Optionally, the aqueous silicate solution can be acidified with strong acid, such as nitric acid, in order to prepare larger silicate anions, such as $Si_2O_5^{2-}$ or $Si_3O_7^{2-}$. Similarly, a soluble metal compound containing the desired metal ion is dissolved in a minimum amount of water to make a second solution. The soluble metal compound can be, for example, a metal nitrate, such as magnesium nitrate, calcium nitrate, or lanthanum nitrate; a metal chloride, such as yttrium chloride; or the like. Likewise, the second solution is heated to boiling to facilitate dissolution of the soluble metal compound. The two solutions are mixed and a precipitate forms of the desired metal silicate catalyst. The catalyst is filtered and dried by methods known in the art.

Optionally, any of the metal silicate catalysts can be made insoluble by application to a support material. Any support material is acceptable provided that it does not enhance the formation of undesirable cyclic products in the process of this invention. Suitable supports include any refractory oxide such as alumina (hydrated and dehydrated forms), zirconia, boria, thoria, magnesia, titania, tantala, chromia, silica, kielselguhr, and mixtures of these materials. Preferably, the support material is silica, alumina, or titania. The support material typically has a surface area of at least about $0.1 \text{ m}^2/\text{g}$. Preferably, the support material has a surface area in the range from about $5 \text{ m}^2/\text{g}$ to about $600 \text{ m}^2/\text{g}$, most preferably in the range from about $50 \text{ m}^2/\text{g}$ to about $200 \text{ m}^2/\text{g}$. These surface areas are measured by the Brunauer-Emmett-Teller (BET) method, as described by R. B. Anderson, in *Experimental Methods in Catalytic Research*, Academic Press, 1968, pp 48-66.

The metal silicate catalyst can be applied to the support material in any known fashion, such as by impregnation or by precipitation in situ from the catalyst preparation reaction. In these preparations the silicate is adsorbed onto the support. Alternatively, the silicate can be prepared on the support. In this preparation a catalyst precursor compound, such as identified hereinbefore, is applied to the support to yield a catalyst precursor chemically bound to the support. For example, magnesium chloride can be calcined on a silica support. The bound catalyst precursor can then be converted into the silicate catalyst by reaction with a soluble silicate salt, or by hydrolyzing and calcining.

The amount of catalyst which is employed in the process of this invention is any amount which is effective in producing the desired mixtures of polyalkylenepolyamines and alkanolpolyamines. The amount of catalyst varies considerably depending upon the specific reactants and reaction conditions employed. Typically, the amount of catalyst is in the range from about 0.1 weight percent to about 20 weight percent based on the weight of reactant amine. Preferably, the amount of catalyst is in the range from about 1 weight percent to about 15 weight percent based on the weight of reactant amine.

The process of this invention can be carried out in any suitable reactor, including batch reactors, continuous fixed-bed reactors, slurry reactors, fluidized bed reactors, and catalytic distillation reactors. Preferably, the reactor is a continuous fixed-bed reactor.

The difunctional aliphatic alcohol and amine reactants are contacted with the catalyst at any operable temperature which promotes the amination process of this invention and yields the desired mixture of polyalkylenepolyamines and alkannolpolyamines. Typically, the temperature is in the range from about 200° C. to about 350° C. Preferably, the temperature is in the range from about 250° C. to about 325° C. More preferably, the temperature is in the range from about 260° C. to about 315° C. Below the preferred lower temperature the conversion of difunctional alcohol may be low. Above the preferred upper temperature the selectivity for higher molecular weight cyclic polyalkylenepolyamines and the corresponding hydroxy compounds may increase.

Likewise, the difunctional aliphatic alcohol and amine reactants are contacted with the catalyst at any operable pressure which promotes the amination process of this invention and yields the desired mixture of polyalkylenepolyamines and alkanolpolyamines. Typically, the pressure is sufficient to maintain the reactants in the liquid state at the temperature of the reaction. Preferably, the pressure is in the range from about atmospheric to about 4000 psig. More preferably, the pressure is in the range from about 100 psig to about 3000 psig. Most preferably, the pressure in the range from about 400 psig to about 2000 psig. In batch reactors the pressure is autogenous, and depends upon the vapor pressure of the reactants and products, and on the temperature of the reaction.

When the process is conducted in a continuous flow reactor, the flow rate of the reactants can be varied. Generally, the difunctional aliphatic alcohol and the reactant amine are premixed to form a feed stream which is fed into the reactor at any operable stream which is fed into the reactor at any operable flow rate which yields the desired mixture of polyalkylenepolyamines and alkanolpolyamines. The flow rate is expressed as the liquid hourly space velocity (LHSV) and is given in units of grams of total reactants per milliliter of total reactor volume per hour, $g\ ml^{-1}\ hr^{-1}$. It is preferred to employ a liquid hourly space velocity of reactants in the range from about $0.1\ g\ ml^{-1}\ hr^{-1}$ to about $10.0\ g\ ml^{-1}\ hr^{-1}$, more preferably in the range from about $0.5\ g\ ml^{-1}\ hr^{-1}$ to about $4.0\ g\ ml^{-1}\ hr^{-1}$. It should be understood that the space velocity controls the residence time of the reactants in the continuous flow reactor.

When the process of this invention is conducted in a batch reactor, the reaction time determines the length of contact between the reactants and the catalyst. Any reaction time which yields the desired mixture of polyalkylenepolyamines and alkanolpolyamines is acceptable. The reaction time depends upon the quantity of reactants, the quantity of catalyst, the temperature of the reaction and desired degree of conversion. Preferably, the reaction time in a batch reactor is in the range from about 1 hour to about 20 hours.

When the difunctional aliphatic alcohol and the reactant amine are contacted in accordance with the process of this invention, a reaction occurs to form a mixture of products comprising polyalkylenepolyamines and alkanolpolyamines. For example, in one aspect the hydroxyl moiety of the difunctional alcohol reacts with the reactant amine yielding the polyalkylenepolyamine product, and water is eliminated as a by-product. For difunctional alcohol can react with the reactant amine yielding the alkanolpolyamine product, and ammonia is eliminated as a by-product. Hence, a mixture of polyalkylenepolyamine and alkanolpolyamine is produced. For example, monoethanolamine reacts with ethylenediamine to yield a mixture of diethylenetriamine and N-(2-aminoethyl)ethanolamine, also known as (hydroxyethyl)ethylenediamine. In the special case where the difunctional alcohol contains two hydroxyl moieties, the reactant amine may react first at one hydroxyl to yield an alkanolpolyamine, which in turn may react with a reactant amine to yield a polyalkylenepolyamine. For example, when ethylene glycol and ethylenediamine are contacted, the products include a mixture of triethylenetetramine and (hydroxyethyl)ethylenediamine. Thus, a mixture of polyalkylenepolyamines and alkanolpolyamines is formed.

A variety of polyalkylenepolyamine and alkanolpolyamine mixtures, which otherwise would be difficult to prepare, is simply and directly available by the process of this invention. For example, mixtures of triethylenetetramine and (hydroxyethyl)diethylenetriamine can be prepared in one-step by the process of this invention by (a) reacting diethylenetriamine with monoethanolamine, or (b) reacting ethylenediamine with (hydroxyethyl)ethylenediamine. Compared with the prior art, the process of this invention is considerably more cost effective.

The polyalkylenepolyamine and alkanolpolyamine products are higher homologues of the reactants, meaning that the product mixture possesses on the average a higher molecular weight than the reactant mixture.

Preferably, the product of this invention is a mixture of polyalkylenepolyamines and alkanolpolyamines enriched in non-cyclic products, such as straight-chain or branched chain compounds. For example, if the reactants are monoethanolamine and ethylenediamine, the polyalkylenepolyamine products are preferably diethylenetriamine and linear and branched triethylenetetramines; and the corresponding alkanolpolyamines such as (hydroxyethyl)ethylenediamine, and linear and branched (hydroxyethyl)diethylenetriamines.

The preferred non-cyclic polyalkylenepolyamines can be represented by the general formula:

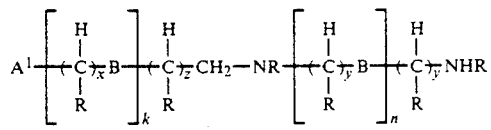

wherein B, R, x, y, z, k, and n are defined hereinbefore; and wherein $A^1$ is NHR or:

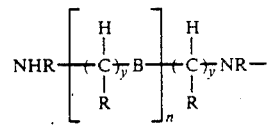

Preferably, R is hydrogen. More preferably, R is hydrogen, $A^1$ is $NH_2$, k is 0, y is 2, and z is 1. Most preferably, R is hydrogen, $A^1$ is $NH_2$, k is 0, y is 2, z is 1, and n is 1, 2, or 3; thus, the polyalkylenepolyamines are diethylenetriamine, triethylenetetramine, and tetraethylenepentamine.

The preferred non-cyclic alkanolpolyamines can be represented by the same general formula, as shown hereinabove, with the exception that $A^1$ is OH. Preferably, R is hydrogen. More preferably, R is hydrogen, k is 0, y is 2, and z is 1. Most preferably, R is hydrogen, k is 0, y is 2, z is 1, and n is 1, 2, or 3; thus, the alkanolpolyamines are (hydroxyethyl)ethylenediamine, (hydroxyethyl)diethylenetriamines, and (hydroxyethyl) triethylenetetramines.

For the purposes of this invention, "conversion" is defined as the weight percentage of difunctional aliphatic alcohol lost from the feed stream as a result of reaction. The conversion can vary widely depending upon the reactants, the form of the catalyst, and the process conditions such as temperature, pressure, and flow rate. Within the preferred temperature range, as the temperature increases the conversion generally increases. Within the preferred space velocity range, as the space velocity increases the conversion generally decreases. Typically, the conversion of the difunctional alcohol is at least about 3 weight percent. Preferably, the conversion is at least about 10 weight percent, more preferably at least about 20 weight percent, even more preferably at least about 30 weight percent, and most preferably at least about 45 weight percent.

Likewise, for the purposes of this invention "selectivity" is defined as the weight percentage of converted difunctional alcohol which forms a particular polyalkylenepolyamine or alkanolpolyamine product. Typically, the selectivities also vary widely depending upon the reactants, the form of the catalyst, and the process conditions. Typically, the process of this invention achieves high selectivities to non-cyclic polyalkylenepolyamines or alkanolpolyamines. Within the preferred temperature range, as the temperature increases the selectivity for non-cyclic products generally decreases. Within the preferred space velocity range, as the space velocity increases the selectivity for non-cyclic products generally increases. At temperatures above the preferred range and space velocities below the preferred range, the selectivities for cyclic compounds may increase. Preferably, the combined selectivities to all non-cyclic products is at least about 30 weight percent, more preferably, at least about 50 weight percent, even more preferably at least about 70 weight percent, and most preferably at least about 85 weight percent.

The product mixture obtained in the process of this invention is usually separated by distillation methods. Each of the polyalkylenepolyamine fractions, which is recovered via distillation, contains linear, branched and/or cyclic homologues. The linear and branched homologues are referred to simply as "non-cyclic" products. For each polyalkylenepolyamine fraction there is a corresponding alkanolpolyamine fraction, wherein a hydroxyl moiety is substituted for one of the terminal amine moieties of the polyalkylenepolyamine. (Vide supra) The alkanolpolyamine fraction also contains linear, branched and/or cyclic homologues. The extent to which the product mixture contains alkanolpolyamines is readily apparent in the weight ratio of alkanolpolyamines to polyalkylenepolyamines for a particular fraction. This ratio is identified by the notation $[OH/NH_2]_f$. For example, when a triethylenetetramine fraction (TETA) is produced in accordance with this invention, the notation $[OH/NH_2]_f$ for this fraction refers to the weight ratio of (hydroxyethyl)diethylenetriamine (HEDETA) to triethylenetetramine (TETA). Typically, the weight ratio of alkanolpolyamines to polyalkylenepolyamines is at least about 0.10. Preferably, the weight ratio of alkanolpolyamines to polyalkylenepolyamines is at least about 0.20, more preferably, at least about 0.40, even more preferably, at least about 0.60, and most preferably, at least about 0.80.

The following examples illustrate the invention, but are not intended to be limiting thereof. All percentages are given as weight percent, unless noted otherwise. In some instances the following abbreviations are used to indicate the reactants and products:

| | |
|---|---|
| MEA | monoethanolamine |
| EG | ethylene glycol |
| EDA | ethylenediamine |
| AEEA | N-(2-aminoethyl)ethanolamine or (hydroxyethyl)ethylenediamine |
| DETA | diethylenetriamine |
| TETA | triethylenetetramine |
| HEDETA | (hydroxyethyl)diethylenetriamine |
| TEPA | tetraethylenepentamine |
| HETETA | (hydroxyethyl)triethylenetetramine |
| PEHA | pentaethylenehexamine |
| HETEPA | (hydroxyethyl)tetraethylenepentamine |
| HEHA | hexaethylheptamine |
| HEPEHA | (hydroxyethyl)pentaethylhexamine |
| PIP | piperazine |
| AEP | N-(2-aminoethyl)piperazine |
| HEP | N-hydroxyethylpiperazine |
| C. | Cyclic |
| NC. | Non-cyclic (includes linear and branched compounds) |
| $[OH/NH_2]_f$ | weight ratio of alkanolpolyamines to polyalkylenepolyamines for a specific distillation fraction |

EXAMPLE 1

(a) Preparation of Thorium Silicate Catalyst

Sodium silicate, $Na_2SiO_3.9H_2O$ (284.8 g; 1.00 moles) is dissolved in 1200 ml of water and heated to 80° C. to form a solution. Concentrated nitric acid (63 ml) is slowly added to the solution such that no precipitate forms during the addition. The acidified solution is heated to boiling, and the volume is raised to 2000 ml with water. Thorium nitrate, $Th(NO_3)_4.4H_2O$ (138.4 g; 0.25 moles), is dissolved in 2000 ml of water at boiling to form a second solution. The hot, acidified silicate solution is added to the hot thorium nitrate solution with stirring at a rate of 100 ml per minute to yield a precipitate. The supernatant and the precipitate are heated with stirring at boiling for about 3 hours, then cooled overnight at room temperature. The precipitate is filtered. The filtered solid is washed three times with about 2000 ml of water, and refiltered. The filtercake is dried at 150° C. for about 15 hours and calcined at 300° C. for about 15 hours to yield a particulate catalyst of thorium silicate.

(b) Process Using Thorium Silicate Catalyst

The catalyst (25 g), prepared hereinabove, is loaded into a stainless steel, tubular, fixed-bed continuous flow reactor (approximately 6 inches × 0.5 inch diameter). A feedstream comprising monoethanolamine and ethylenediamine in an EDA/MEA mole ratio of 2/1 is fed upward through the catalyst for several days at a temperature of 310° C., a pressure of 1405 psig, and a liquid hourly space velocity of 1.4 $hr^{-1}$. The reaction products are analyzed by gas-liquid chromatography (gc). A CAM (Carbowax amine deactivated) capillary column (30 m × 0.25 mm dia.) is employed for the analysis of total amines. Isomer distributions are determined on an SE-54 capillary column (30 m × 0.25 mm dia.). A 15 meter DB-5 is used for total amine and isomer analyses. The conversion of monoethanolamine is 47 percent, and the selectivities are set forth in Table I.

TABLE I

| Ethyleneamine Fraction | % Selectivity Ethyleneamine[1] (% NC)[2] | Ethanolamine Fraction | % Selectivity Ethanolamine[1] (% NC)[2] | [OH/NH₂]f Ratio |
|---|---|---|---|---|
| DETA | 32 (100) | AEEA | 10 (100) | 0.31 |
| TETA | 20 (80) | HEDETA | 8 (87) | 0.40 |
| TEPA | 12 (83) | HETETA | 3 (100) | 0.25 |
| PEHA | 2 (99) | HETEPA | — | — |
| PIP | 6 | — | — | — |

[1] AEP and HEP elute as one peak with a total peak area percentage of 5.
[2] % NC refers to the weight percentage of non-cyclic products in the specified fraction.

It is seen that thorium silicate catalyzes the reaction of monoethanolamine with ethylenediamine to mixtures of higher molecular weight polyethylenepolyamines and ethanolpolyamines with minimal cyclic products.

EXAMPLE 2

The catalyst of Example 1 is employed in the reaction of aminoethylethanolamine with ethylenediamine. The reactants are fed into the reactor of Example 1 in an EDA/AEEA mole ratio of (a) 2:1, (b) 2:1, and (c) 4:1 with the results set forth in Table II.

TABLE II (a)

| Ex. 2 | EDA/AEEA | Temp. °C. | Press. psig | LHSV hr⁻¹ | % AEEA Conversion |
|---|---|---|---|---|---|
| (a) | 2 | 280 | 1405 | 1.3 | 36 |
| (b) | 2 | 312 | 1399 | 1.2 | 82 |
| (c) | 4 | 300 | 1311 | 1.4 | 55 |

TABLE II (b)

| Ethyleneamine Fraction | % Selectivity Ethyleneamine[1] (% NC)[2] 2a | 2b | 2c | Ethanolamine Fraction | % Selectivity Ethanolamine[1] (% NC)[2] 2a | 2b | 2c | [OH/NH₂]f Ratio 2a | 2b | 2c |
|---|---|---|---|---|---|---|---|---|---|---|
| DETA | 8 | 15 | 12 | AEEA[3] | — | — | — | — | — | — |
| TETA | 36 (83) | 29 (83) | 25 (68) | HEDETA | 13 (92) | 13 (65) | 13 (77) | 0.36 | 0.52 | 0.54 |
| TEPA | 11 (82) | 14 (71) | 14 (71) | HETETA | 15 (100) | 8 (81) | 9 (78) | 1.36 | 0.57 | 0.64 |
| PEHA | 2 (100) | 8 (75) | 12 (83) | HETEPA | 1 (100) | 4 (76) | 2 (100) | 0.5 | 0.33 | 0.25 |
| PIP | 10 | 7 | 6 | — | — | — | — | — | — | — |

[1] AEP and HEP elute as one peak in the gas chromatograph, with a total peak area percentage of (a) 3, (b) 5, and (c) 6.
[2] % NC refers to the weight percentage of non-cyclic products in the specified fraction.
[3] AEEA is a component of the feedstream.

It is seen that thorium silicate catalyzes the reaction of aminoethylethanolamine with ethylenediamine to a mixture of predominantly non-cyclic, higher molecular weight polyethylenepolyamines and ethanolpolyamines.

EXAMPLE 3

(a) Preparation of Magnesium Silicate Catalyst

Sodium silicate, Na₂SiO₃.9H₂O (180.0 g; 0.63 moles), is dissolved in 1200 ml of water, and the resulting solution is heated to 80° C. Concentrated nitric acid (40 ml) is added to the hot solution slowly such that no precipitate is formed. The acidified solution is heated to boiling and the volume is raised to 2000 ml with water. Magnesium nitrate, Mg(NO₃)₂.6H₂O (81.0 g; 0.32 moles) is dissolved in 2000 ml of water, and the resulting solution is heated to boiling. The hot sodium silicate solution is added with rapid stirring to the magnesium nitrate solution at a rate of 100 cc/minute. A precipitate forms. The supernatant liquid and the precipitate are heated and stirred for about 3 hours at boiling, then cooled overnight at room temperature. The precipitate is filtered, washed three times with about 2000 ml of water and refiltered. The filtercake is then dried for about 15 hours at 150° C. and calcined for about 15 hours at 300° C. to yield a particulate catalyst of magnesium silicate.

(b) Reaction Using Magnesium Silicate Catalyst

A feed stream containing aminoethylethanolamine and diethylenetriamine in a DETA/AEEA mole ratio of 1:1 is passed over the magnesium silicate catalyst (15.7 g) in the manner described in Example 1. The process conditions and results are set forth in Table III.

TABLE III (a)

| Ex. 3 | DETA/AEEA | Temp. °C. | Press. psig | LHSV hr⁻¹ | % AEEA Conversion |
|---|---|---|---|---|---|
| (a) | 1 | 280 | 1405 | 0.8 | 71 |
| (b) | 1 | 260 | 1405 | 0.8 | 36 |

TABLE III (b)

| Ethyleneamine Fraction | % Selectivity Ethyleneamine[1] (% NC)[2] 3a | 3b | Ethanolamine Fraction | % Selectivity Ethanolamine[1] (% NC)[2] 3a | 3b | [OH/NH₂]f Ratio 3a | 3b |
|---|---|---|---|---|---|---|---|
| EDA | 9 | 5 | MEA | 5 | tr. | 0.56 | — |
| TETA | 15 | 16 | HEDETA | 9 | 5 | 0.60 | 0.31 |

TABLE III (b)-continued

| Ethylene amine Fraction | % Selectivity Ethyleneamine[1] (% NC)[2] | | Ethanol amine Fraction | % Selectivity Ethanolamine[1] (% NC)[2] | | [OH/NH$_2$]$_f$ Ratio | |
|---|---|---|---|---|---|---|---|
| | 3a | 3b | | 3a | 3b | 3a | 3b |
| TEPA | (27) 18 | (24) 32 | HETETA | (33) 8 | (38) 17 | 0.44 | 0.53 |
| PEHA | (50) 11 | (82) 8 | HETEPA | (75) 4 | (92) 1 | 0.36 | 0.13 |
| HEHA | (45) 1 | (52) — | HEPEHA | (25) 3 | (53) — | 3.0 | — |
| PIP | (100) 7 | 10 | — | (100) — | — | — | — |

[1] AEP and HEP elute as one peak with a total area percentage of 5 for both 3a and 3b.
[2] % NC refers to the weight percentage of non-cyclic products in the specified fraction.

The data show that magnesium silicate catalyzes the reaction of aminoethylethanolamine with diethylenetriamine to a mixture of higher molecular weight polyethylenepolyamines and ethanolpolyamines.

EXAMPLE 4

The magnesium silicate catalyst of Example 3 is employed in the reaction of monoethanolamine with diethylenetriamine. The process conditions and results are set forth in Table IV (Examples 4a and 4b). A magnesium silicate catalyst, prepared as described in Example 3 with the exception that the catalyst is calcined at 500° C., is employed in the reaction of monoethanolamine and diethylenetriamine, as set forth in Table IV (Example 4c).

TABLE IV (a)

| Ex. 4 | DETA/MEA | Temp. °C. | Press. psig | LHSV hr$^{-1}$ | % MEA Conversion |
|---|---|---|---|---|---|
| (a) | 2 | 275 | 1393 | 2.0 | 25 |
| (b) | 0.5 | 280 | 1411 | 1.0 | 72 |
| (c) | 0.5 | 265 | 1405 | 1.1 | 35 |

TABLE IV (b)

| Ethyleneamine Fraction | % Selectivity Ethyleneamine[1] (% NC)[2] | | | Ethanol-amine Fraction | % Selectivity Ethanolamine[1] (% NC)[2] | | | [OH/NH$_2$]$_f$ Ratio | | |
|---|---|---|---|---|---|---|---|---|---|---|
| | 4a | 4b | 4c | | 4a | 4b | 4c | 4a | 4b | 4c |
| DETA[3] | — | — | — | AEEA | 7 (100) | 9 (100) | 10 (100) | — | — | — |
| TETA | 32 (81) | 19 (53) | 19 (70) | HEDETA | 10 (100) | 15 (73) | 15 (100) | 0.31 | 0.79 | 0.78 |
| TEPA | 34 (88) | 21 (62) | 18 (77) | HETETA | — | 7 (71) | 15 (85) | — | 0.33 | 0.24 |
| PEHA | — | 8 (63) | 2 (100) | HETEPA | — | 2 (50) | 4 (62) | — | 0.25 | — |
| HEHA | — | 1 (100) | — | HEPEHA | — | 1 (100) | — | — | 1.0 | — |
| PIP | 10 | 8 | 7 | — | — | — | — | — | — | — |

[1] AEP and HEP elute as one peak with a total area percentage of (4a) 8, (4b) 10 and (4c) 7.
[2] % NC refers to the weight percentage of non-cyclic products in the specified fraction.
[3] DETA is a component of the feedstream.

The data show that magnesium silicate catalyzes the reaction of monoethanolamine with diethylenetriamine to a mixture of higher molecular weight polyethylenepolyamines and ethanolamines of predominantly non-cyclic products.

We claim:

1. A process of preparing a mixture of polyalkylenepolyamines and alkanolpolyamines comprising contacting a reactant mixture containing a difunctional aliphatic alcohol and a primary or secondary aliphatic amine with a catalytic amount of a catalyst consisting essentially of a Group IIA metal silicate or an actinide metal silicate, the contacting occurring under reaction conditions such that a product mixture of polyalkylenepolyamines and alkanolpolyamines is formed, such that the product mixture possesses a higher average molecular weight than the reactant mixture.

2. The process of claim 1 wherein the difunctional aliphatic alcohol is represented by the formula:

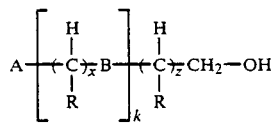

wherein A is OH or NHR; each B is independently NR or O; each R is independently hydrogen, an alkyl moiety of $C_1$-$C_{12}$ carbon atoms, a $C_1$-$C_{12}$ hydroxyalkyl or aminoalkyl moiety, or phenyl or tolyl; x is an integer from 2 to about 12; k is an integer from 0 to about 150; and z is an integer from 1 to about 12.

3. The process of claim 2 wherein R is hydrogen, x is 2 and z is 1.

4. The process of claim 2 wherein R is hydrogen, k is 0, z is 1, and the difunctional aliphatic alcohol is monethanolamine.

5. The process of claim 2 wherein the difunctional alcohol is N-(2-aminoethyl)ethanolamine.

6. The process of claim 1 wherein the reactant amine is an alkylenepolyamine represented by the formula:

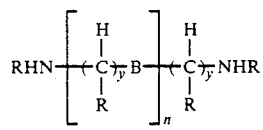

wherein each B is independently NR or O; each R is independently hydrogen, an alkyl moiety of $C_1-C_{12}$ carbon atoms, a $C_1-C_{12}$ hydroxyalkyl or aminoalkyl moiety, or phenyl or tolyl; each y is independently an integer from 2 to about 12; and n is an integer from 0 to about 150.

7. The process of claim 6 wherein B is NR and R is hydrogen.

8. The process of claim 7 wherein B is NR, R is hydrogen, each y is 2 and the alkylenepolyamine is an ethylenepolyamine.

9. The process of claim 8 wherein the alkylenepolyamine is ethylenediamine.

10. The process of claim 1 wherein the mole ratio of aliphatic amine to difunctinal aliphatic alcohol is in the range from about 0.1 to about 20.

11. The process of claim 1 wherein the metal silicate is a Group IIA silicate.

12. The process of claim 1 wherein the metal silicate is magnesium silicate.

13. The process of claim 1 wherein the metal silicate is a silicate of an actinide metal.

14. The process of claim 13 wherein the metal silicate is thorium silicate.

15. The process of claim 1 wherein the temperature is in the range from about 200° C. to about 350° C.

16. The process of claim 1 wherein the pressure is in the range from about atmospheric to about 4000 psig.

17. The process of claim 1 wherein the liquid hourly space velocity is in the range from about 0.1 g ml$^{-1}$ hr$^{-1}$ to about 10.0 g ml$^{-1}$ hr$^{-1}$.

18. The process of claim 1 wherein the polyalkylenepolyamine product is represented by the formula:

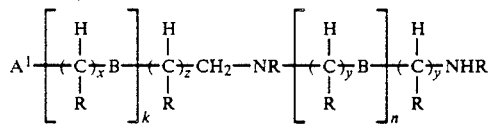

wherein each B is independently NR or O; each R is independently hydrogen, an alkyl moiety having from $C_1-C_{12}$ carbon atoms, a hydroxyalkyl or aminoalkyl moiety having from $C_1-C_{12}$ carbon atoms, or phenyl or tolyl; x and y are each independently integers from 2 to about 12; z is an integer from 1 to about 12; k and n are each independently integers from 0 to about 150; and wherein $A^1$ is NHR or:

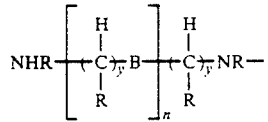

19. The process of claim 18 wherein R is hydrogen, $A^1$ is $NH_2$, k is 0, y is 2, z is 1, and n is 1, 2, or 3.

20. The process of claim 1 wherein the alkanolpolyamine is represented by the general formula:

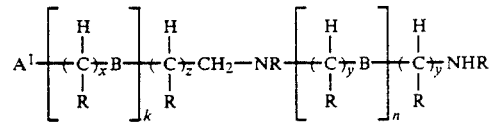

wherein each B is independently NR or O; each R is independently hydrogen, an alkyl moiety having from $C_1-C_{12}$ carbon atoms, a hydroxyalkyl or aminoalkyl moiety having from $C_1-C_{12}$ carbon atoms, or phenyl or tolyl; x and y are each independently integers from 2 to about 12; z is an integer from 1 to about 12; k and n are each independently integers from 0 to about 150; and wherein $A^1$ is OH.

21. The process of claim 1 wherein the weight ratio of alkanolpolyamines to polyalkylenepolyamines is at least about 0.10.

22. The process of claim 1 wherein the weight ratio of alkanolpolyamines to polyalkylenepolyamines is at least about 0.40.

23. The process of claim 1 wherein the weight ratio of alkanolpolyamines to polyalkylenepolyamines is at least about 0.60.

24. The process of claim 1 wherein the weight ratio of alkanolpolyamines to polyalkylenepolyamines is at least about 0.80.

25. A process of preparing a mixture of polyethylenepolyamines and ethanolpolyamines comprising contacting a mixture of an ethanolamine and an ethylenediamine in the presence of a catalyst consisting essentially of magnesium silicate or thorium silicate at a temperature in the range from about 250° C. to about 325° C., a pressure in the range from about 400 psig to about 2000 psig, a liquid hourly space velocity in the range from about 0.5 g ml$^{-1}$ hr$^{-1}$ to about 4.0 g ml$^{-1}$ hr$^{-1}$, such that a product mixture of ethanolpolyamines and ethylenepolyamines is formed wherein the average molecular weight of the product mixture is greater than the average molecular weight of the reactant mixture and wherein the weight ratio of alkanolpolyamines to polyalkylenepolyamines is at least about 0.10.

* * * * *